(12) United States Patent
Park

(10) Patent No.: US 7,587,073 B2
(45) Date of Patent: Sep. 8, 2009

(54) METHOD AND APPARATUS FOR A MEDICAL IMAGE PROCESSING SYSTEM

(75) Inventor: Jong-Won Park, Daejeon (KR)

(73) Assignee: Virtual ITech Co., Ltd., Daejeon (KR)

( * ) Notice: Subject to any disclaimer, the term of this patent is extended or adjusted under 35 U.S.C. 154(b) by 738 days.

(21) Appl. No.: 10/487,649

(22) PCT Filed: Aug. 27, 2002

(86) PCT No.: PCT/KR02/01618

§ 371 (c)(1),
(2), (4) Date: Nov. 4, 2004

(87) PCT Pub. No.: WO03/017833

PCT Pub. Date: Mar. 6, 2003

(65) Prior Publication Data

US 2005/0078857 A1    Apr. 14, 2005

(30) Foreign Application Priority Data

Aug. 31, 2001  (KR) .............................. 2001-53346
May 21, 2002   (KR) .............................. 2002-28073

(51) Int. Cl.
*G06K 9/00* (2006.01)
(52) U.S. Cl. .................. 382/128; 382/132; 382/236; 382/180; 600/408; 600/407; 348/699
(58) Field of Classification Search .................. 382/128

See application file for complete search history.

(56) References Cited

U.S. PATENT DOCUMENTS

| 5,542,003 | A * | 7/1996 | Wofford ..................... 382/132 |
| 5,838,827 | A * | 11/1998 | Kobayashi et al. .......... 382/236 |
| 5,873,824 | A * | 2/1999 | Doi et al. .................... 600/408 |
| 5,878,746 | A * | 3/1999 | Lemelson et al. ........... 600/407 |
| 6,380,986 | B1 * | 4/2002 | Minami et al. .............. 348/699 |
| 6,795,578 | B1 * | 9/2004 | Kotani et al. ................ 382/180 |
| 2003/0156747 | A1 * | 8/2003 | Faber .......................... 382/128 |

* cited by examiner

*Primary Examiner*—Samir A. Ahmed
*Assistant Examiner*—Tsung-Yin Tsai
(74) *Attorney, Agent, or Firm*—Nelson Mullins Riley & Scarborough, LLP

(57) ABSTRACT

Disclosed is a medical image processing system comprising a medical image storage server for storing digital image data provided by means such as computerized tomography or magnetic resonance image apparatus in a medical image database; and an image processing system which is coupled to said medical image storage server and to several client computers by TCP/IP protocol; wherein said image processing system comprises a user interface unit which converts the user's command into an electric signal and outputs said electric signal; an image processor unit which reads a medical image out of said medical image database, performs an image processing program comprising a medical image controlling algorithm and outputs a result signal; and an output interface unit which receives said result signal and converts said result signal into a format which can be recognized by a user.

6 Claims, 21 Drawing Sheets

FIG.17a
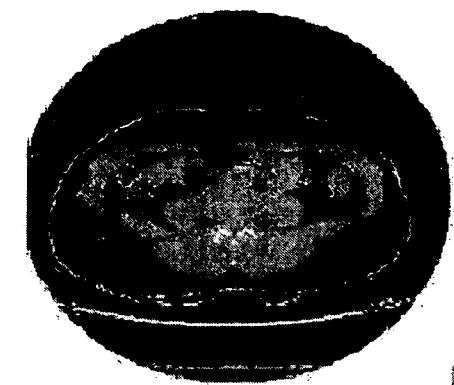
(a) original image
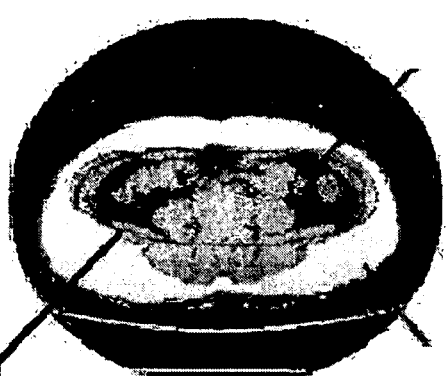
(c) an image in which the panniculum of an organ is separated from the external panniculum
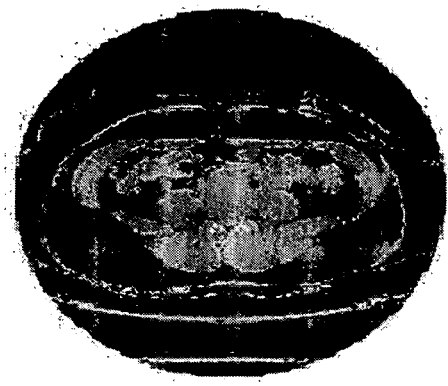
(b) an image from which the panniculum is extracted
panniculum of the organ
ratio    16.46    %
volume   519.102  cc
internal panniculum
ratio    8.23     %
volume   259.553  cc
total panniculum
ratio    24.69    %
volume   778.655  cc

FIG. 17b
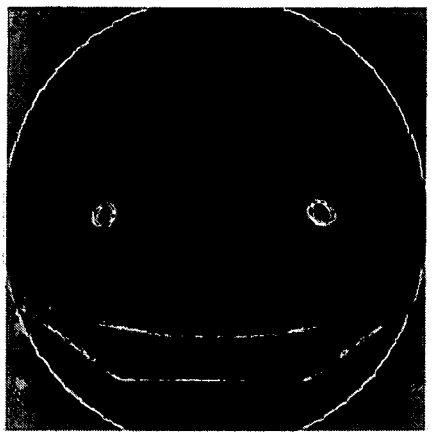
(a) original image
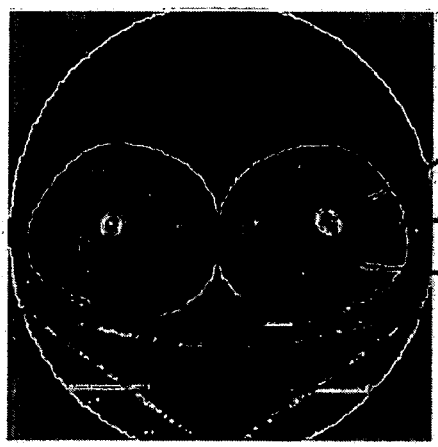
(c) an image from which panniculum, muscles and bones are extracted
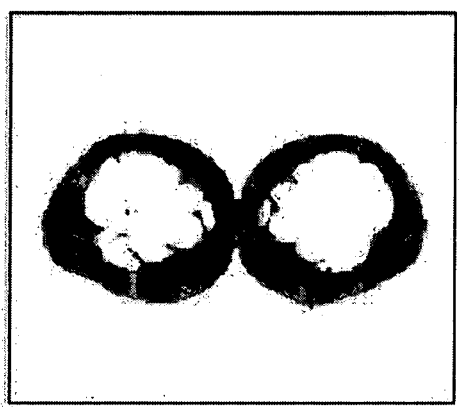
(b) an image from which panniculum is extracted
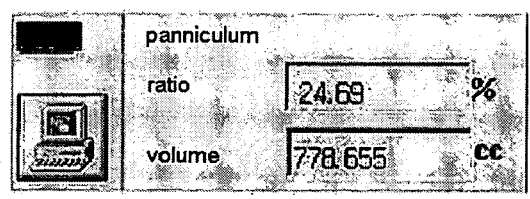

FIG. 19
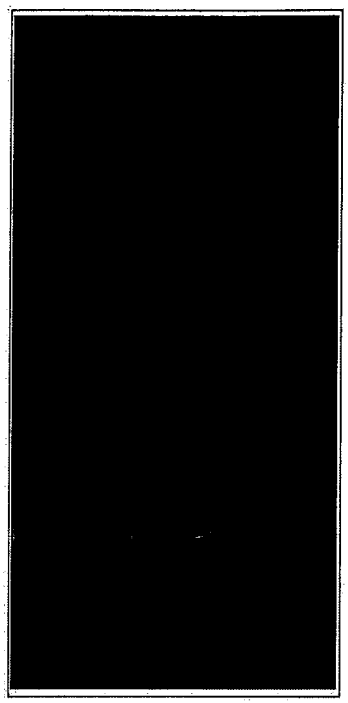  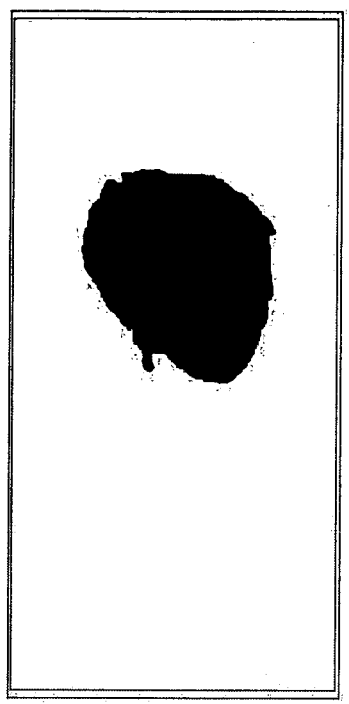
(a) original image  (b) leveled image  (c) an image from which the liver image is eliminated

METHOD AND APPARATUS FOR A MEDICAL IMAGE PROCESSING SYSTEM

TECHNICAL FIELD

The present invention relates to apparatus and method for medical image processing system. In particular, the present invention relates to apparatus and method medical image processing system, by which even people who have little knowledge about image processing can easily acquire desired data from medical images.

BACKGROUND ART

Medical images are acquired from X-ray, computerized tomography(CT), magnetic resonance imaging(MRI), ultrasonic, etc., and different apparatus is used according to the part of a body or the object of observation. Medical images have an advantage of observing inside of a body without cutting a body open, and widely used for deciding a schedule or a method of a diagnosis, treatment and an operation. Additional information about such medical images should be supplied to those who analyzes and diagnoses such medical images for an objective decision. Employing computerized digital image processing method, such additional information, which enables quicker and more accurate analysis and diagnosis, can be supplied to medical people. These medical image processing techniques are growing rapidly and widespread, and more efficient and accurate processing techniques are being developed.

To acquire desired data from an image, numerous processing steps are required. Methods developed to have new algorithms based on medical expert knowledge should be applied instead of using the conventional image processing methods, for medical images have their unique features. These new algorithms have been developed to be operated by text commands on workstations with UNIX operating systems. Therefore, expert knowledge about image processing and UNIX computer systems was required in order to operate a conventional medical image processing system. Moreover, conventional image processing systems have been developed to deal with ordinary digital image processing. However, conventional image processing systems are inefficient to deal with medical images because medical images need different image processing methods from those applied to ordinary images. The number of medical images for diagnosis or treatment is so enormous that using conventional image processing systems requires too long processing time and too much operating efforts. There have been difficulties for those who have little knowledge about image processing to acquire desired data from conventional image processing systems.

SUMMARY OF THE INVENTION

An object of the present invention is to provide a medical image processing system, which is needless of expert knowledge about image processing to operate.

Another object of the present invention is to provide a medical image processing system, which has a graphic user interface and is based on Microsoft Windows operating system.

To achieve the above object, the present invention comprises a medical image storage server for storing digital image data provided by means such as CT (computerized tomography) or MRI(magnetic resonance imaging) apparatus in a medical image database, and an image processing system which is coupled to said medical image storage server and to several client computers by TCP/IP protocol.

Another detailed feature of the medical image processing system of the present invention is that said image processing system comprises a user interface unit converting the user's command into an electric signal and outputting said electric signal; an image processor unit reading a medical image out of said medical image database, performing an image processing program comprising a medical image controlling algorithm and outputting a result signal; and an output interface unit receiving said result signal and converting said result signal to be a format, which is recognizable to users.

Another detailed feature of the medical image processing system of the present invention is that said image processing program embedded in said image processor comprises both an ordinary digital image processing algorithm and an organ-searching algorithm.

The medical image processing method of the present invention comprises the steps of providing a menu screen as a window frame on a display means; converting a command of a user, which is received through an input interface unit, into a control signal and transferring said control signal to an image processor unit; analyzing said control signal; loading an image corresponding to said control signal and displaying said image on a displaying means; receiving an image processing control signal from a user; reading an image processing algorithm embedded in said image processor and performing said algorithm; displaying a result image acquired by performing said algorithm on a displaying means; and storing the result data, which is obtained according to the command of the user, in a specific database.

BRIEF DESCRIPTION OF DRAWINGS

FIG. 17a illustrates an extraction of panniculum of an abdomen, and FIG. 17b illustrates an extraction of panniculum of a leg.

FIGS. 19(a),(b) and (c) are cross sectional views of a liver of a swine acquired by computerized tomography apparatus for calculating a volume of the liver.

BEST MODE FOR CARRYING OUT THE INVENTION

Figure 1:
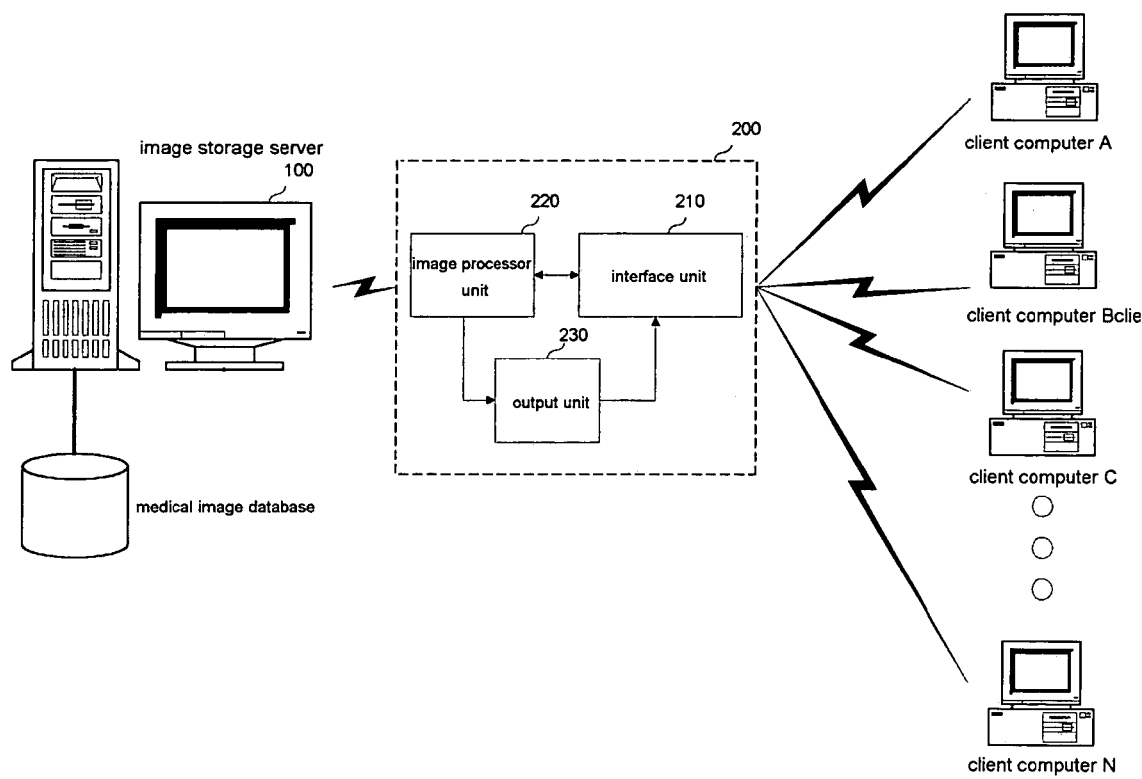
FIG. 1 is a block diagram showing a structure of a medical image processing system of the present invention.

Hereafter, apparatus and method of a medical image processing system of the present invention is fully described referring to the attached figures.

Those who operate a medical image processing system are roughly divided into two groups:

The first group consists of medical people, who use medical images for diagnosis and medical research. They are more interested in the medical images and the acquired data from image processing than a digital image processing method itself. The object of their using a medical image processing system is to acquire more objective and accurate information from medical images, more easily.

The other group consists of developers, who develop more efficient new algorithms for medical image processing. They check medical images on the screen, selectively employ a develop algorithm and understand features like pixel values, brightness values, etc. of medical images. Medical images have different features from ordinary digital images, and the feature varies according to the kind of organs. Therefore, general features of medical images are important for developing a new image processing algorithm. A developer improves a medical image processing system by confirming the result data, which are acquired from a new algorithm, with the aid of medical people having expert knowledge about medical science and medical images and by adding a new algorithm to the medical image processing system.

A medical image processing system should be developed for both of these two groups to be able to do a required task and to add new functions into the medical image processing system. The medical image processing system of the present invention is developed using an object-oriented development method, which first embodies basic functions and continually improves the system by adding new functions that users want.

The requirements of medical people to a medical image processing system are as follows:
1. The system should be able to extract from an image file a specific image of an organ that is selected by a user.
2. The system should be able to calculate the volume of the extracted organ.
3. The system should be able to color organs with different colors according to the range of the brightness of a medical image file.
4. The system should be developed on an ordinary Microsoft Windows platform so that the system can be operated easily without a complicated instruction about how to operate.

The requirements of developers to a medical image processing system are as follows:
1. Information data from a medical image file should be easily acquired. Image leveling and image histogram should be displayed on the screen, and data should be easily acquired from the image.
2. Algorithms that are used for extracting an image of a specific organ should be easily reused for finding an image of another organ.
3. Each algorithm should be independently applied to a new image file.
4. Results of image processing should be stored as a form of a file and reused later again.
5. A newly developed algorithm should be easily added to a system in order to improve the system.

There are several problems for satisfying the above requirements.

One of those problems is a problem related to the format of medical image files. For there is no standard file format for medical images, images taken by various means are stored as various file formats. For example, a computerized tomography image includes information about photographying method, the size of an image, an encryption key and the name of a patient. For it is difficult to directly apply an ordinary image processing technique to a computerized tomography image, the image should be converted into a standard image file format, to which digital image processing technique is easily applied.

For a program for providing a graphic user interface (GUI) generally has a complicated structure, when such a program is developed with a program for an image processing, each of these programs should be developed to construct an independent class. Owing to an encapsulization technique, which provides the minimum interface between the two classes, the interference between the two programs can be reduced, the program can be debugged more easily, and the system can be simply managed and improved. A medical image processing system of the present invention is developed on the Microsoft Windows platform aiming to process medical images graphically on the Windows environment.

As seen in FIG. 1, the medical image processing system of the present invention comprises a medical image storage server 100 for storing digital image data provided by means such as computerized tomography or magnetic resonance image apparatus in a medical image database and an image processing system 200 which is coupled to said medical image storage server 100 and to several client computers by TCP/IP protocol.

Said image processing system 200 comprises a user interface unit 210 which converts user's command into an electric signal and outputs said electric signal, an image processor unit 220 which reads a medical image out of said medical image database, performs an image processing program including a medical image controlling algorithm and outputs a result signal, and an output interface unit 230 which receives said result signal and converts said result signal into a format which user can recognize.

In the image processing system of the present invention, graphic data are transformed sequentially to be displayed on a program window. Not all of the graphic data are displayed on the program window, but specific data are displayed according to the size of an activated program window and the resolution of the screen.

The class, which constructs the medical image processing system, constructs the application program with 4 objects.

The first object is a program window part concerning the visual frame such as title bars, system menus, condition bars, scroll bars, etc.

The second object is a client part concerning text, graph and the output result.

The third object is a data processing part concerning memory loading and data processing.

The fourth object is a management part concerning managing the above three parts.

The program should be mainly programmed centering round these parts by using the classes registered in the library. By operating the menu of this program, the program synchronizes, generates necessary dialogues or program windows, and performs necessary processing steps. The result of image processing is displayed on a displaying means for recognition of a user. A graphic interface may be constructed with a standard object by an object oriented developing method. An image processing program can combine a static structure of a characteristic information of an image and an action conducted in reference to the conditional change of the image into one object. As for an image processing algorithm, it can be defined as one of the action conducted by an image object, but it is desirable that an image processing algorithm be separated from an image object in order to diminish complexity of the program for continual improvement of algorithm and management of the program. Moreover, although each algorithm may be defined as an individual object, all the algorithms may also be defined as one class in view of removing duplicated methods and attributes of the algorithms.

When image processing is performed to the medical image object displayed on the screen, changes of the condition of the image object may be classified into two groups; one by an ordinary digital image processing algorithm and the other by an organ-searching algorithm.

Digital image processing algorithm changes the condition of an image object when the image is leveled and colored. When the image is leveled, the image data in the memory is changed according to an image leveling algorithm, and the result is displayed on a screen. Image coloring does not alter the stored image data into gray image data of 256 levels, instead alters the palette value for representing colors to determine the colors of the image, and the image is displayed on the screen. The histogram just reads an original image data, calculates values and displays the result data of calculation on the screen as a graph, not altering the image object in the memory. Therefore, the current image object can maintain its original data and always shows the same histogram. The histogram can be provided with any of 256 color images or monotone images at any processing step.

Organ-searching algorithms should be sequentially applied to the image data, otherwise the desired result cannot be acquired. When organ-searching algorithms are applied, a series of algorithms can be applied all together, and the corresponding result can be observed respectively while applying the algorithms step by step. To observe the result of each step, the color-changing or histogram mentioned above can be used to understand the features of the image. Under development, the combination of algorithms can be altered. In a single image object, the algorithm itself changes the data of an object or just utilizes said data. In this occasion, the result data is transferred to the next calculation step, altering the condition of the image object or not. Therefore, altering the image data is represented to become another condition, while not altering the image data but just calculating by using the image data is expressed to maintain the original condition.

The graphic user interface unit of the medical image processing system of the present invention is developed by Microsoft Visual C++ version 6.0 so as to be operated on the 32 bit operating systems such as Windows NT version 4.0, Windows 95 and Windows 98 on a personal computer. The basic algorithm of the medical image processing system of the present invention is developed by C programming language, and converted into Visual C++. The frame of the user interface unit is a basic frame provided by Visual C++ and it offers a familiar interface to users, which is widely used in ordinary commercial programs.

The interface of the conventional image processing system is one that uses text type commands to operate each step of image processing algorithm. Every image processing step opens an image file, performs an image processing by applying an algorithm to the image file and stores the processed image as a file in order to be used at the next step. The processed image is displayed by another program that works as a graphic viewer. On the contrary, the image processing system of the present invention itself displays the processed image on the screen and an additional graphic viewer is not necessary. Because the processed image is stored as a file and usable at the next step, the load of the system due to input/output process may be diminished and the space for storage may be saved.

Figure 2:
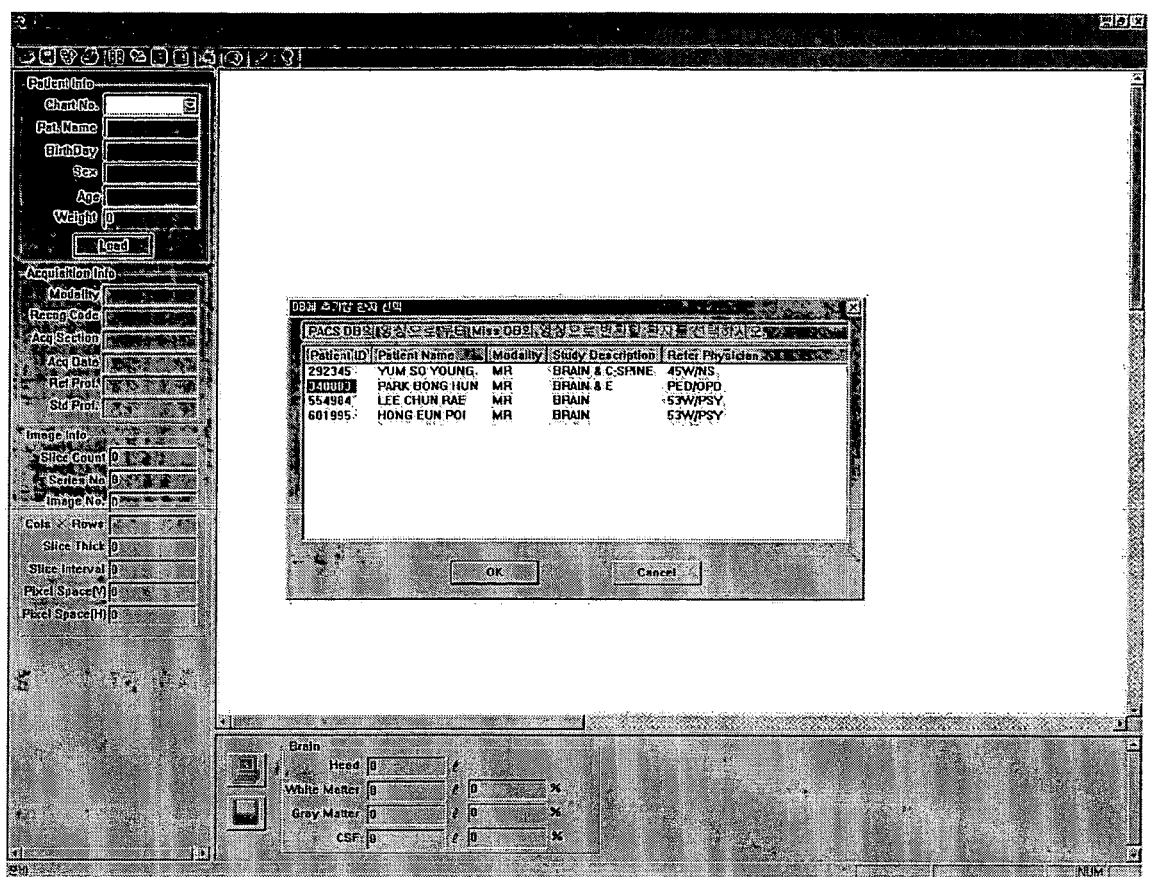
FIG. 2 to FIG. 7 illustrates screen shots whereon image processing of the present invention is performed.
Figure 3:
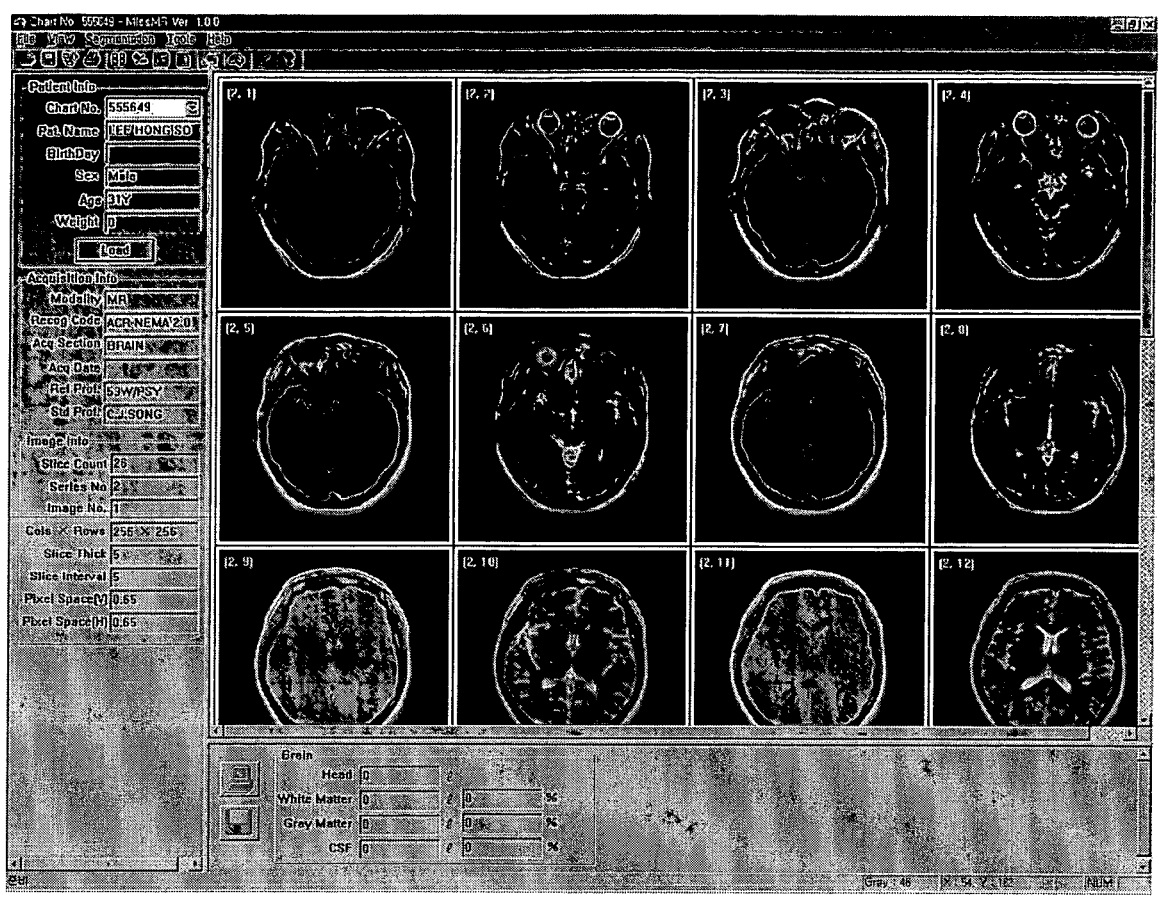
Figure 4:
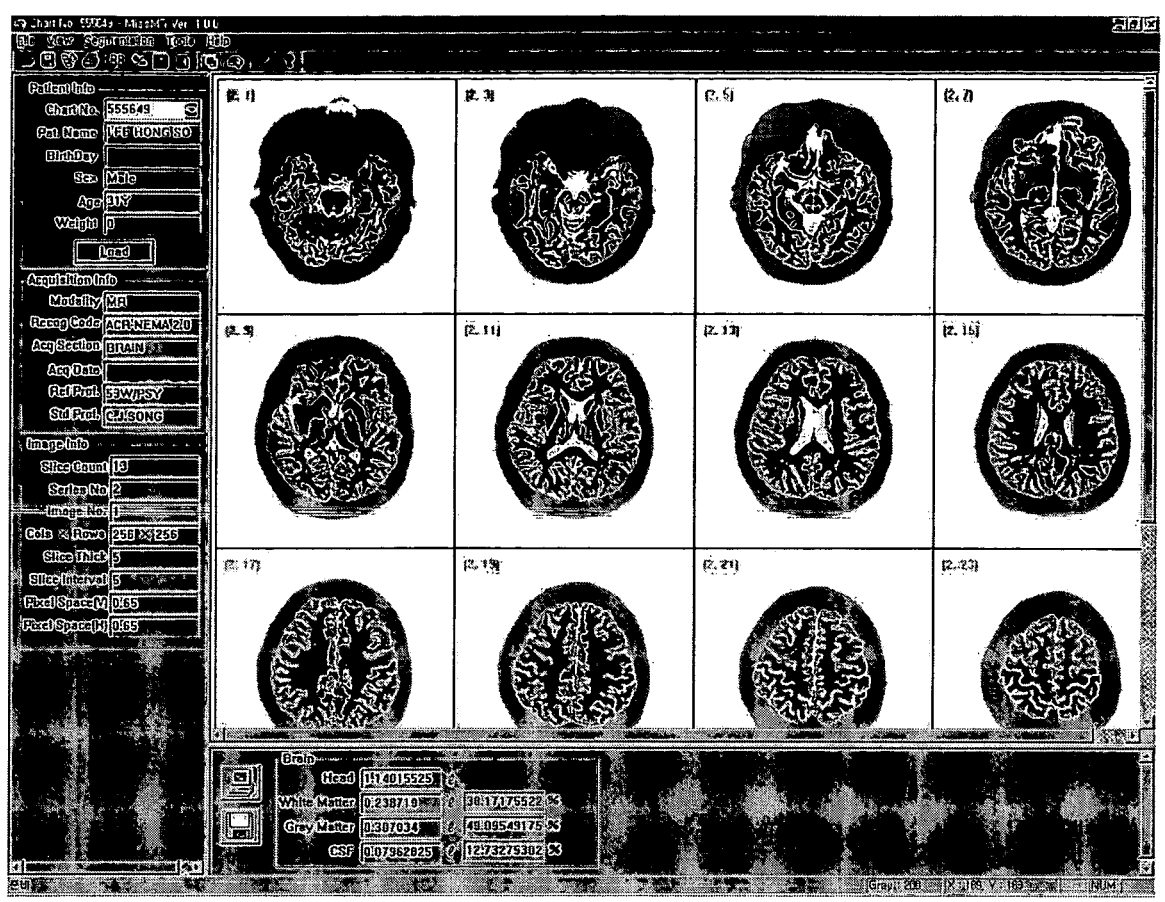

FIG. 2 is a screen shot that illustrates a menu in which a list of patients is read from a medical image database coupled to the medical image storage server 100, and one of the patients is selected. In the case that the patient has a problem with his/her brain or the image of his/her brain is required, as seen in FIG. 3, the image data of the brain of the patient is read. FIG. 3 is a proton image and T2-emphasized image of a brain. Next, in the case that separated images of substantia alba, substantia grisea and cerebrum is respectively required from a client computer, the image processing processor, which received that command through the interface unit, operates an algorithm corresponding to the received command and provides the result to the client computer as seen in FIG. 4.

Figure 5:
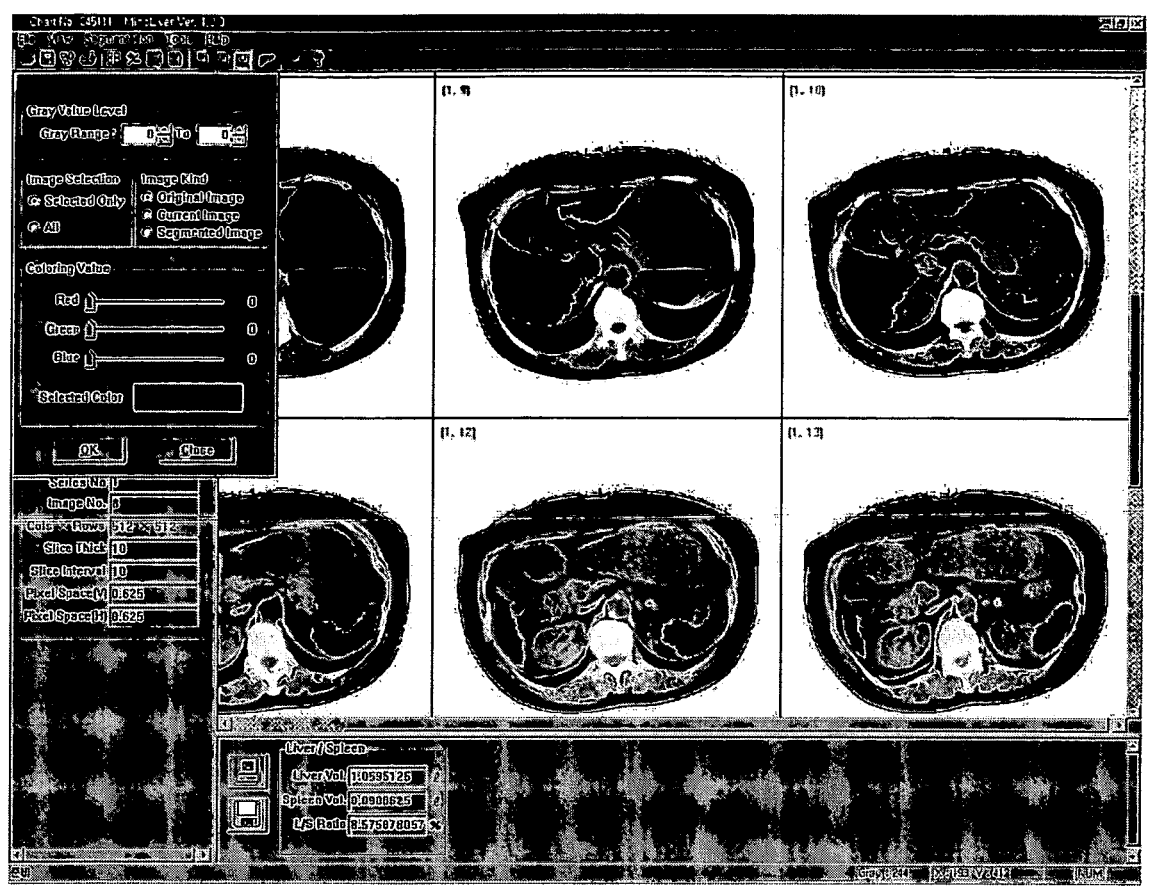
Figure 6:
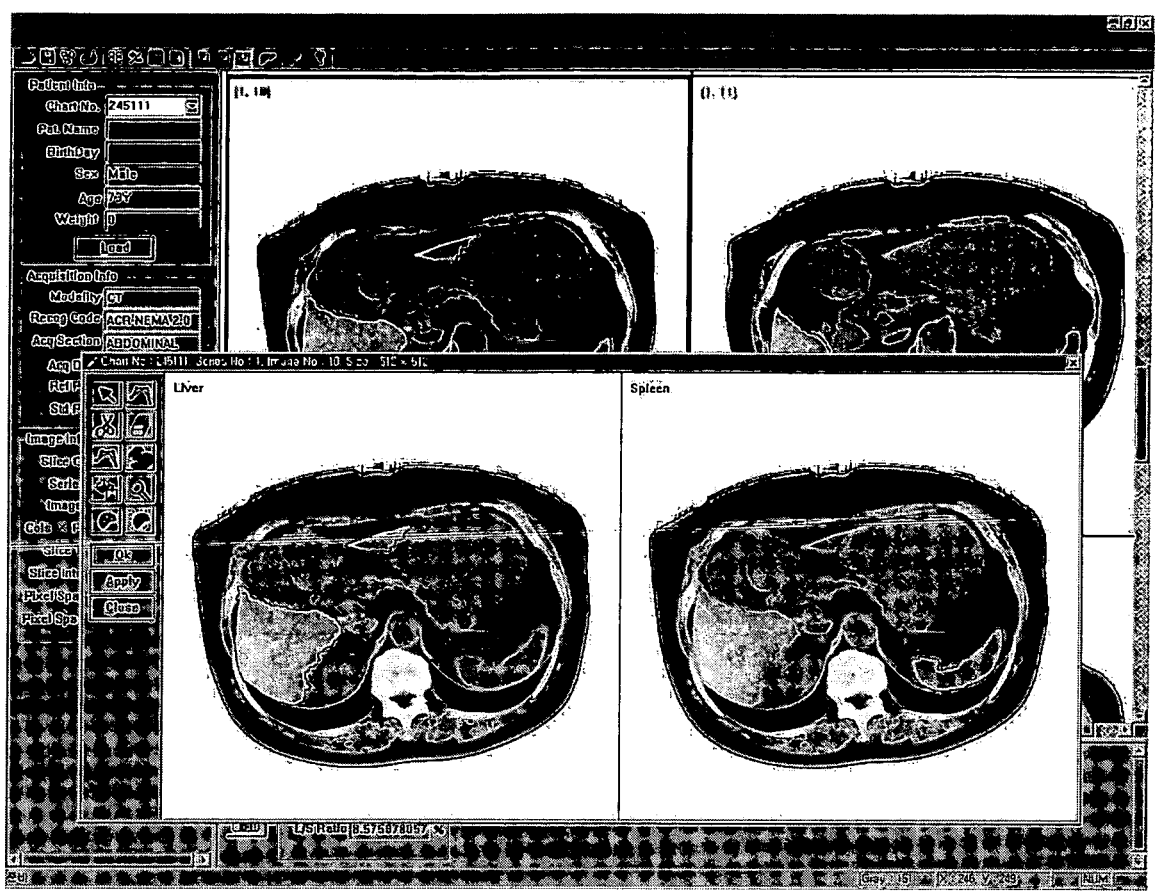
Figure 7:
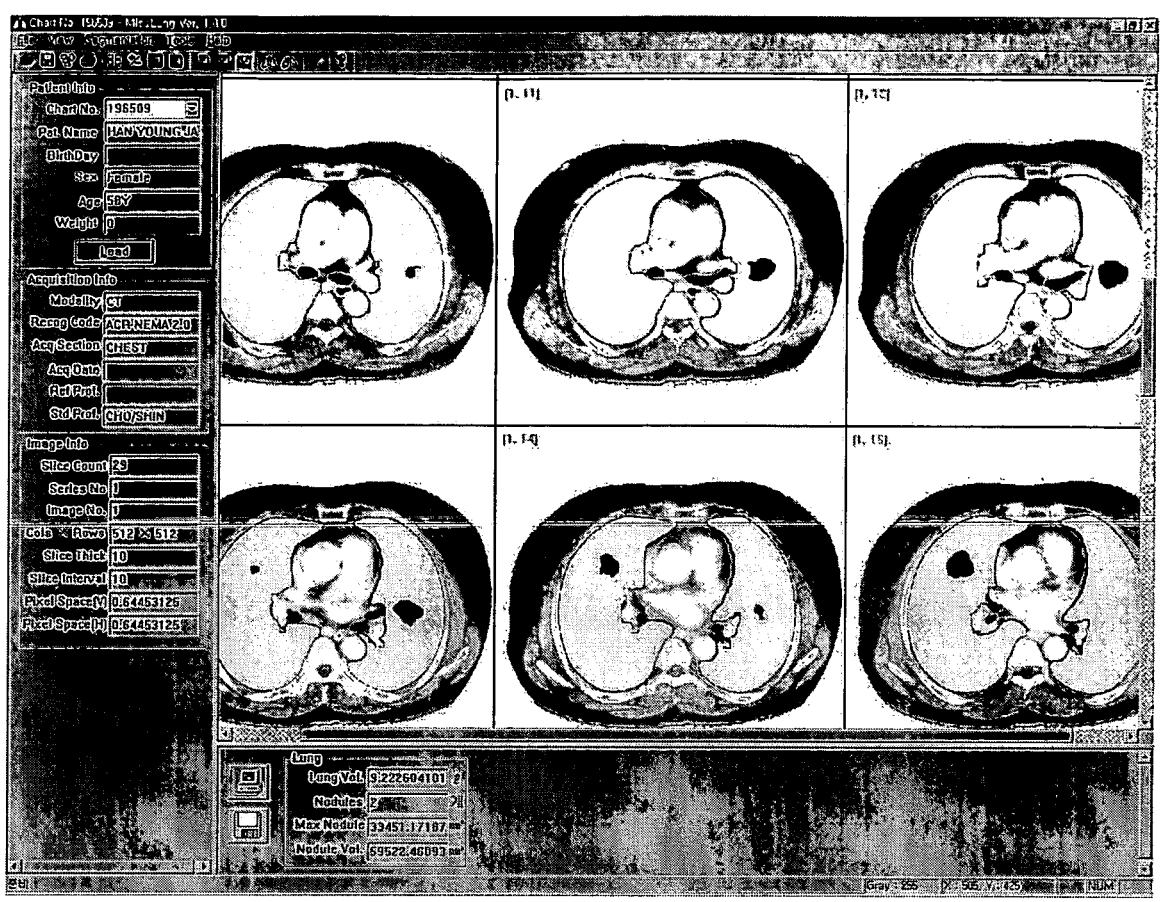

FIG. 5 illustrates a screen shot concerning another embodiment, which is acquired by reading a computerized tomography image data of the abdomen of a patient, separating a liver image and a spleen image and performing a pseudo-coloring. Thereafter, as seen in FIG. 6, a client computer provides a new image with which a detailed manual adjustment can be performed. FIG. 7 illustrates a screen shot concerning another embodiment, which is acquired by extracting an image of a lung and a crystalline lung cancer from a thoracic computerized tomography.

Figure 8:
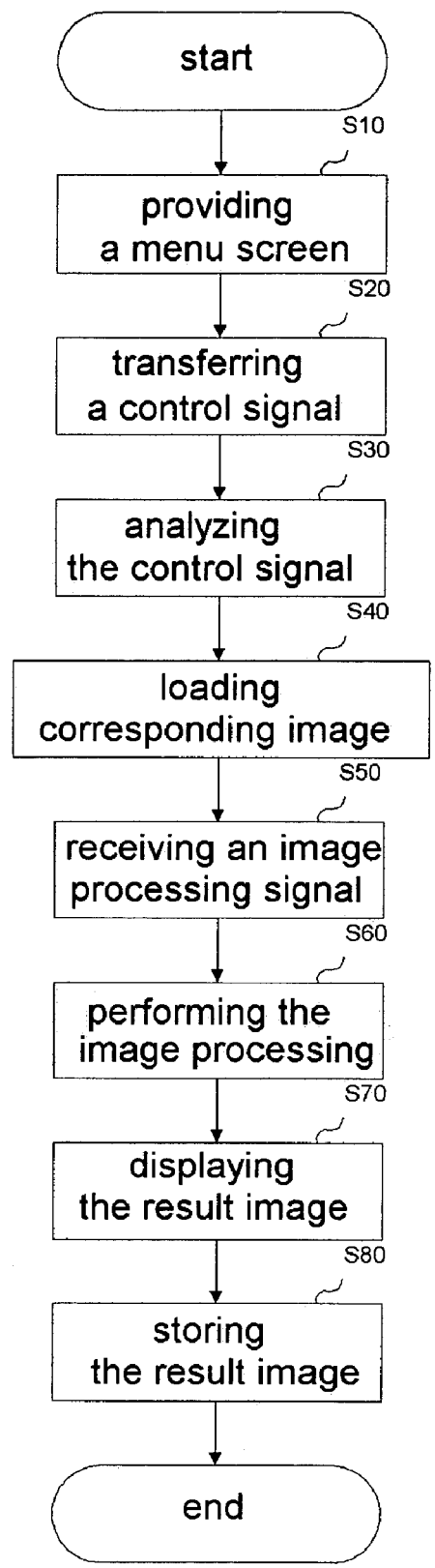
FIG. 8 is a flow diagram illustrating a medical image processing method of the present invention.

As seen in FIG. 8, the medical image processing method comprising the steps of:

(S10) providing a menu screen as a window frame on a display means;

(S20) converting a command of a user, which is received through an input interface unit, into a control signal and transferring said control signal to an image processor unit;

(S30) analyzing said control signal;

(S40) loading an image corresponding to said control signal and displaying said image on a displaying means;

(S50) receiving an image processing control signal from a user;

(S60) reading an image processing algorithm embedded in said image processor and performing said algorithm;

(S70) displaying a result image acquired by performing said algorithm on a displaying means; and (S80) storing the result image, which is obtained according to the command of the user, in a specific database.

The image processing algorithm comprises both ordinary digital image processing algorithms and organ-searching algorithms, and the ordinary digital image processing algorithms comprise an image-leveling algorithm and an image-coloring algorithm.

Hereafter a plurality of preferred embodiments about image processing of organs is described.

Figure 9:
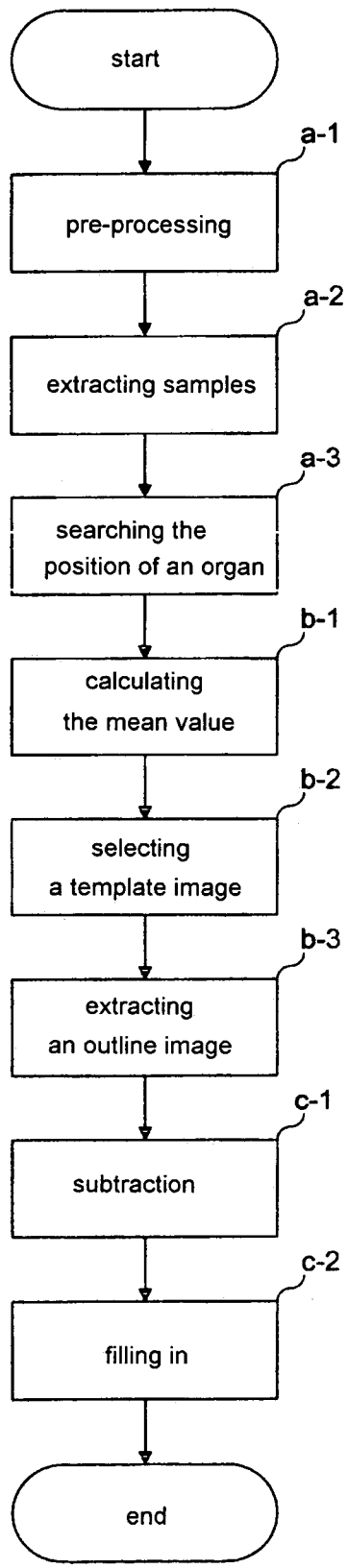
FIG. 9 to FIG. 13 are flow diagrams illustrating image processing algorithms of several organs.

First, as seen in FIG. 9, the organ-searching algorithm for extracting an image of a liver comprises a contrast ratio calculating step A, a template generating step B and an image adjusting step C.

More detailed operating steps are as follows.

A contrast ratio calculating step A comprises a pre-process step a-1, sample extracting step a-2 and position searching step. The pre-process step a-1 further comprises removing a background and removing a muscle layer. The background, the rest part of a body in an image, is processed to have a white color of which the brightness value is 255. Most of computerized tomography images have muscle layers, which have the same brightness value as a liver or a spleen and lie near them, around the body. These muscle layers in the image are removed, because they may be recognized to be a part of organs during pixel tracing and make it difficult to extract a precise organ extraction, consequently occurring an error in the volume calculation of the organ. The panniculum layer and ribs layer may be removed in advance, and the remaining irregular belt-type muscle layers may be removed along the body.

To investigate the distribution of the brightness values, the range of brightness values of organs is estimated, and sample data are extracted. The sample data are concerned to the ratio of the brightness values per unit area.

The contrast ratio calculating step A further comprises a pre-processing step a-1 in which background and muscles of the image is removed to leave organ images only, a sample extracting step a-2 in which the range of brightness values of said organ images is estimated and sample data concerning a ratio of each brightness value of a liver are extracted, and a position searching step a-3 in which the position of a body in each slice is determined and an approximate position of a liver and a spleen of the body is determined thereby acquiring their coordinate value.

The template generating step B further comprises a step b-1 in which a leveled image of an organ is generated and a mean value is calculated by closing a binary image and performing a subtraction between said binary image and said leveled image, a step b-2 in which a template image is selected by comparing a ratio of a brightness value in a mesh of an input image to a ratio of a brightness value of said extracted sample, a subtraction is performed between said leveled image and each of a number of difference images, which are generated according to a difference between said ratio of the brightness value in the mesh of the input image and said ratio of the brightness value of the extracted sample, and a template image is extracted using a mean-value comparison, and a step b-3 in which an image describing the outline of an organ is extracted by opening and enlarging said selected template image.

The image adjusting step C further comprises a step c-1 in which a subtraction is performed on a binary image in order to generate a natural outline without losing information of an original image, and a step c-2 in which the gaps among pixels are recognized and the inside of the organ is filled in without modifying said outline of the organ.

An algorithm for extracting a lung cancer image comprises a lung segmentation step A, a step B in which said boundary image is enlarged using a morphological filter in order that the lung image contains lung cancer tissue, a step C in which the pixels having gray values larger than a predetermined value in said lung segmented image are eliminated and the clusters larger than a predetermined number of pixels are selected to be suspected lung cancer tissues, a step D in which a standard deviation of each pixel is calculated using a histogram of said cluster, which is suspected lung cancer tissue, and a lung cancer extracting step E in which a lung cancer tissue is distinguished from the partial volume.

Figure 10:
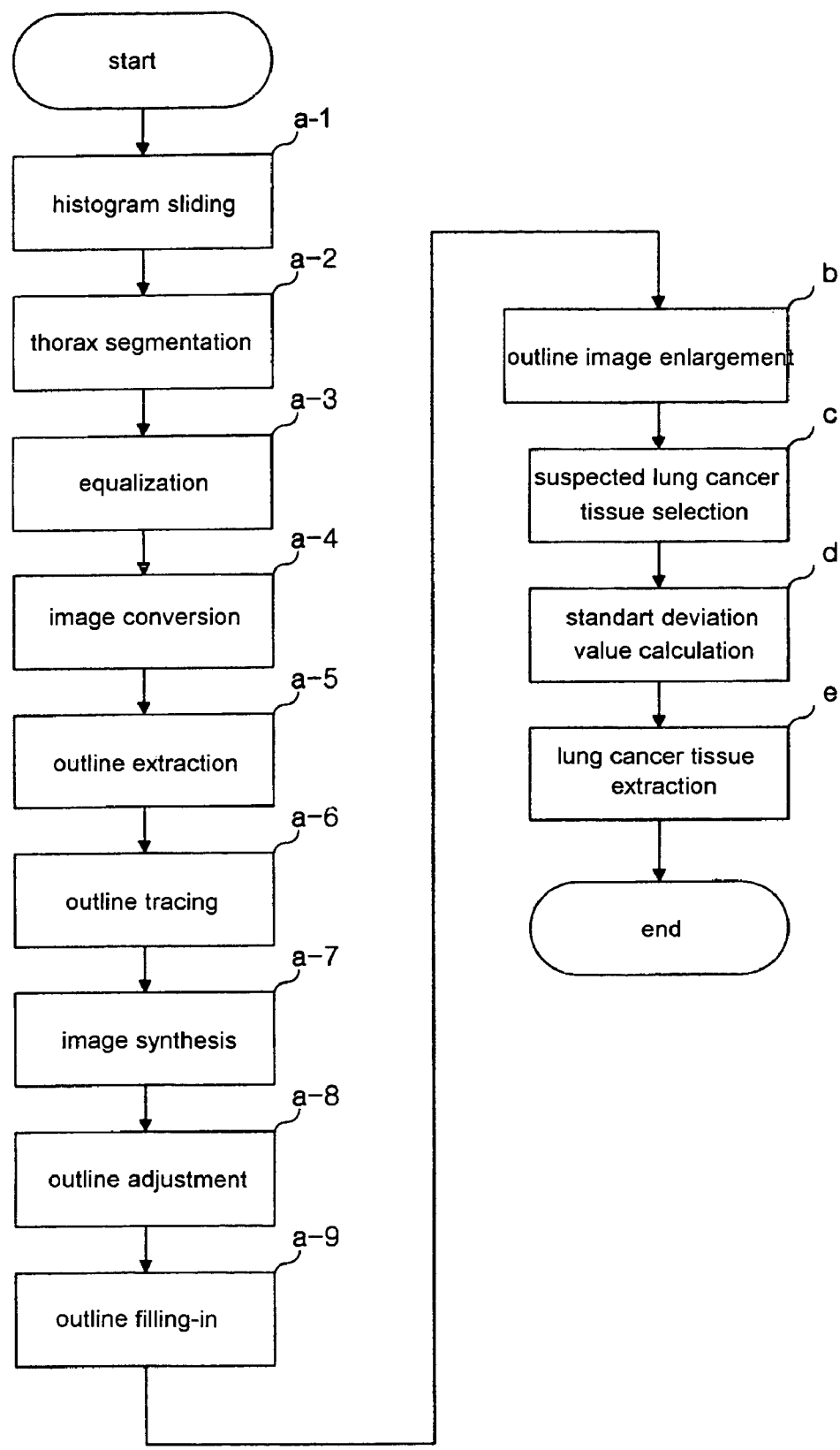

FIG. 10 is a flow diagram illustrating the processing steps.

The lung segmentation step A further comprises a histogram sliding step a-1 in which the gray values of all pixels in an original image are slid by a predetermined offset in order to change the original image brighter, a thorax segmentation step a-2 in which the pixels of the slid image which are darker than a predetermined gray value, are eliminated, an equalization step a-3 in which said thorax segmented image is converted into a histogram-converted image in order to be distributed in all scales, an image conversion step a-4 in which said thorax segmented image is divided into two parts according to a histogram containing frequencies of values of gray levels wherein the mean value becomes a boundary line, a boundary extracting step a-5 in which only a boundary line of said converted image is extracted in order to eliminate a bronchus image from the lung area, a boundary tracing step a-6 in which right and left lungs are eliminated from the bronchus area along said extracted boundary line, an image synthesizing step a-7 in which the original image and the image of said traced boundary line is synthesized, an adjusting step a-8 in which the thickness of said boundary line is adjusted in order to reduce a difference, which occurs when an inside and an outside of each of right and left lung are recognized, and a boundary filling step a-9 in which an inside and an outside of each of right and left lungs are recognizable by assigning predetermined gray values to the pixels, which is inside said boundary line;

An organ-searching algorithm for extracting a kidney image from a computerized tomography image of an abdomen, which is photographed without using a contrast agent, comprises a single slice processing step A and a whole slices processing step B.

Figure 11:
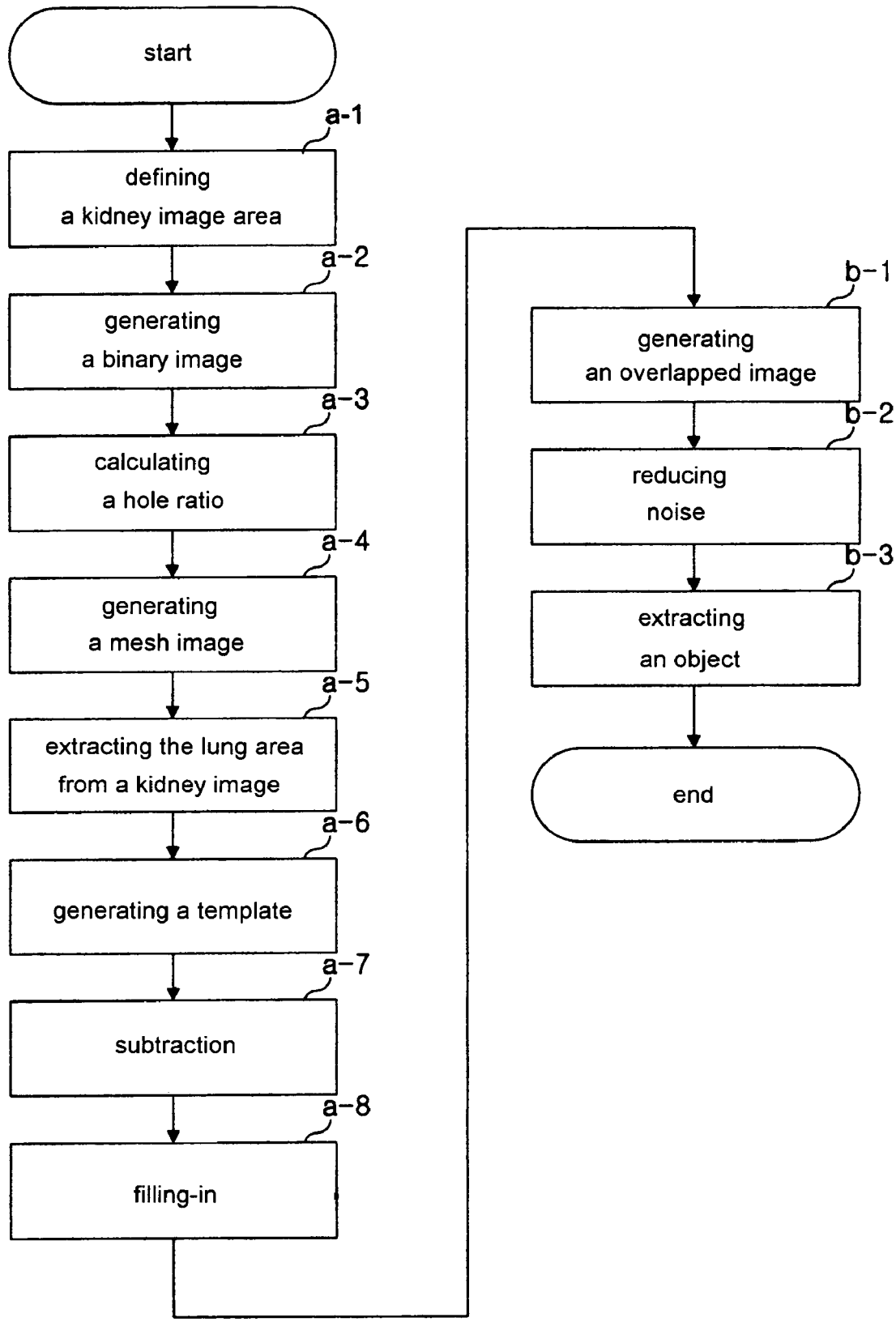

FIG. 11 is a flow diagram illustrating the processing steps.

The single slice processing step further comprise a step a-1 in which an area, which has a contrast value of a predetermined range near a peak value among brightness values of spines in a single slice, is defined as a kidney, a step a-2 in which a binary image is generated by converting the pixels of the images in reference to the threshold value, a step a-3 in which a plurality of pixels and holes are recognized and the ratio of holes to the whole area of kidney is calculated, a step a-4 in which a mesh image is generated by analyzing a relation between the number of holes and said ratio, a step a-5 in which the lung area from said kidney image is extracted in reference to the coordinate values of pixels forming the kidney image, by searching the pixels connected one another lattice-wise, a step a-6 in which a template is generated by enlarging a mesh image of said kidney image, from which lung area is eliminated, and opening the neighboring pixels, a step a-7 in which a subtraction is performed between said template image and said binary image in order to extract from said binary image an area, which corresponds to said template image area, and a step a-8 in which the gaps between pixels of holes inside said subtracted kidney image are recognized and filled in.

The whole slices processing step further comprises a step b-1 in which an overlapped image is generated by adding all the pixel values in each slice processed by said single slice process and a mean value is calculated, a noise reduction step b-2 in which the pixels outside said template image is removed by subtracting template image area excessively enlarged to be larger than said overlapped image, and an object extraction step b-3 in which an object consisting of the largest number of pixels of objects is recognized and extracted.

Figure 12:
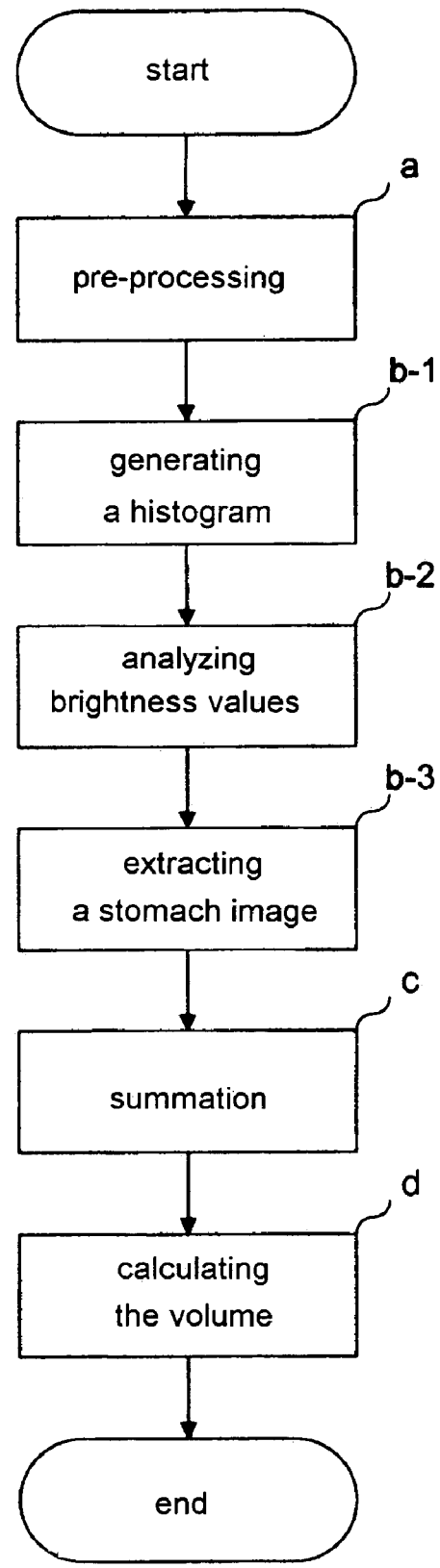

As seen in FIG. 12, an algorithm for calculating a volume of a stomach comprises a pre-processing step A in which a background of an abdomen image is eliminated and said abdomen image is leveled in order to maximize a difference between brightness values in an organ image, a searching step B in which a stomach image, which is divided into a part filled with foodstuffs and the other part filled with air, is extracted by generating histograms of both images, analyzing brightness values and position information, an adding step C in which the stomach areas which are respectively extracted from each histogram are merged, and a volume calculating step D in which the volume of the stomach is calculated using the information stored in an image header of said extracted stomach.

Figure 13:
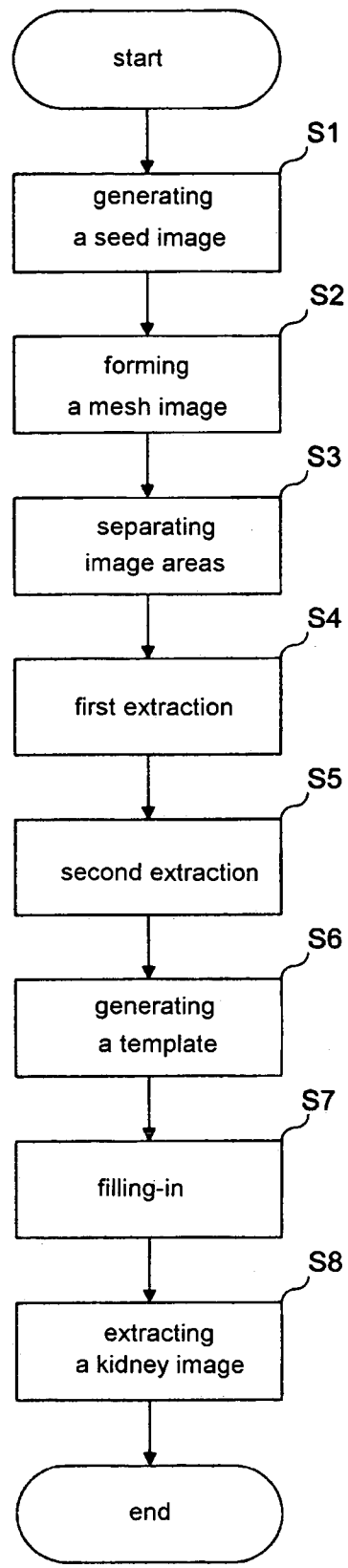
Figure 14:
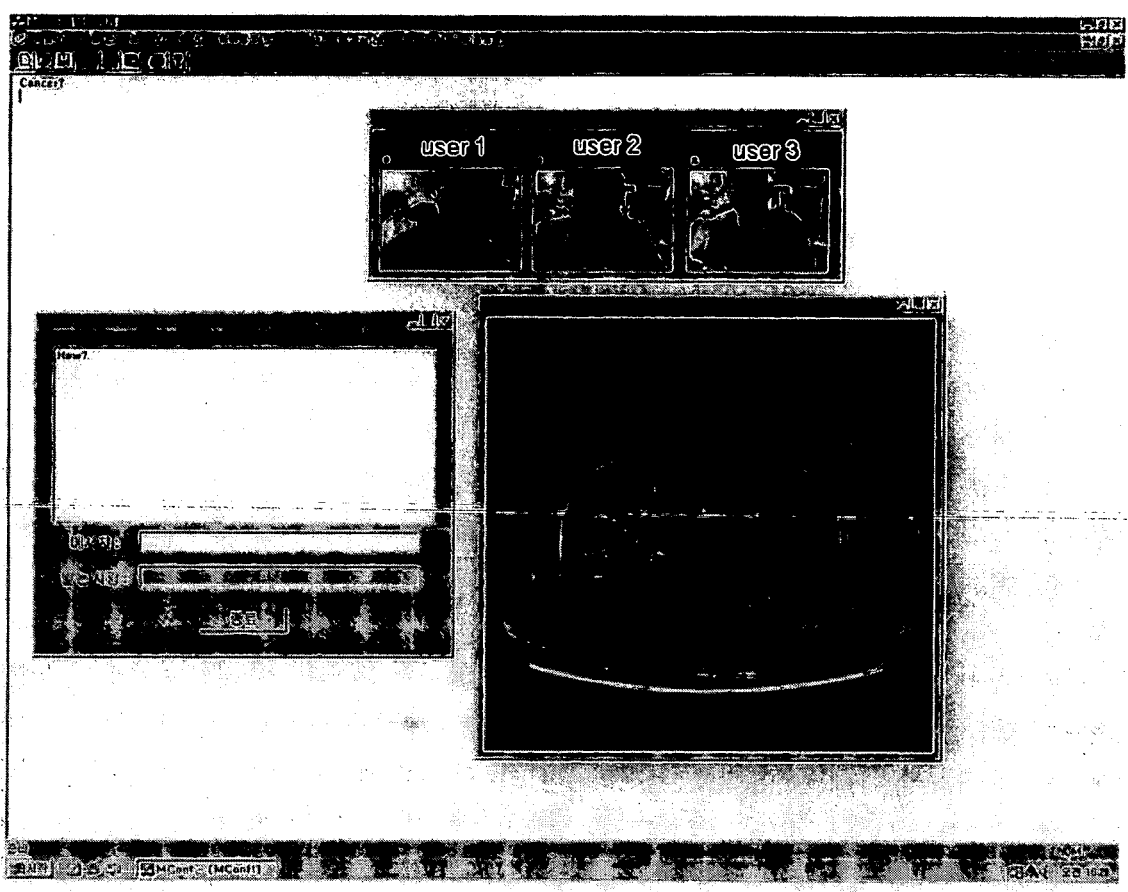
FIG. 14 illustrates a conference function using the medical image processing system of the present invention.

As seen in FIG. 13, an organ-searching algorithm for extracting a liver image from a computerized tomography image of an abdomen, which is photographed using a contrast agent, comprises a step S1 in which a seed image made up of pixels which forms a liver image is generated, a step S2 in which a mesh image of an organ is generated by comparing the distribution of brightness values of an input image in reference to the portion value of said seed image, an area separating step S3 in which a noise area is separated by recognizing a pixel in the lung image and searching for all pixels connected to that pixel, a first extraction step S4 in which an area having a brightness value, which varies from a value of vessel comprising kidney to a mean value of the mesh image, is included in the area of the liver, a second extraction step S5 in which all the holes in the image of the first extraction step are filled, a template generating step S6 in which a template, which is used as a frame for subtracting an organ, which is to be extracted from a binary image, is generated, a filling step S7 in which the gaps between pixels are recognized and small holes inside the organ image are filled, and an extracting step S8 in which the kidney image is extracted from the image containing a kidney image.

Moreover, the medical image processing system of the present invention enables communications among medical people, resulting in decrease of the rate of wrong diagnosis. The result images are transferred to individual client computers of the medical people. The medical people communicate with one another using input devices like keyboards and mice for drawing or for writing. With the aid of movie cameras, microphones and speakers, moving picture images and sound data can also be transferred. With the aid of these means, medical people can discuss the result image of image processing and the rate of wrong diagnosis can be lowered. Here, the supplied medical information may be 3D type images of 2D medical images (computerized tomography, magnetic resonance image, US, etc.) before/after the extraction of a specific organ; or a 3D image can be showed as a 2D image at several angles.

As an extended embodiment, the medical image processing system of the present invention is able to measure the volumes of muscles, panniculum, or bones from data of a computerized tomography image.

To measure the position, volume and ratio of panniculum is very important not only for an aesthetic reason, but also for a health. By now, it is known that an accurate measuring of panniculum should be done with a computerized tomography (CT) or a magnetic resonance image (MRI) apparatus. Although the MRI apparatus doesn't have a danger due to radioactive rays, it has some disadvantages; the MRI apparatus is more expensive than the computerized tomography apparatus and it is hard to measure panniculum accurately due to the change of image data acquired from the MRI image. Moreover, the experts say that computerized tomography is almost harmless to a human body because the amount of the radioactive rays, to which a human body is irradiated, remarkably decreased owing to the development of CT technology. In addition, computerized tomography apparatus can measure the value of panniculum of a body uniformly regardless of the measuring environment, thereby enabling an accurate measurement of the position, volume and ratio of panniculum. Therefore, the medical image processing system of the present invention uses the images photographed by computerized tomography.

By the method of the present invention the panniculum of an abdomen and legs can be measured accurately using the image photographed by computerized tomography. The panniculum of another part of a body can be also measured.

Figure 15:
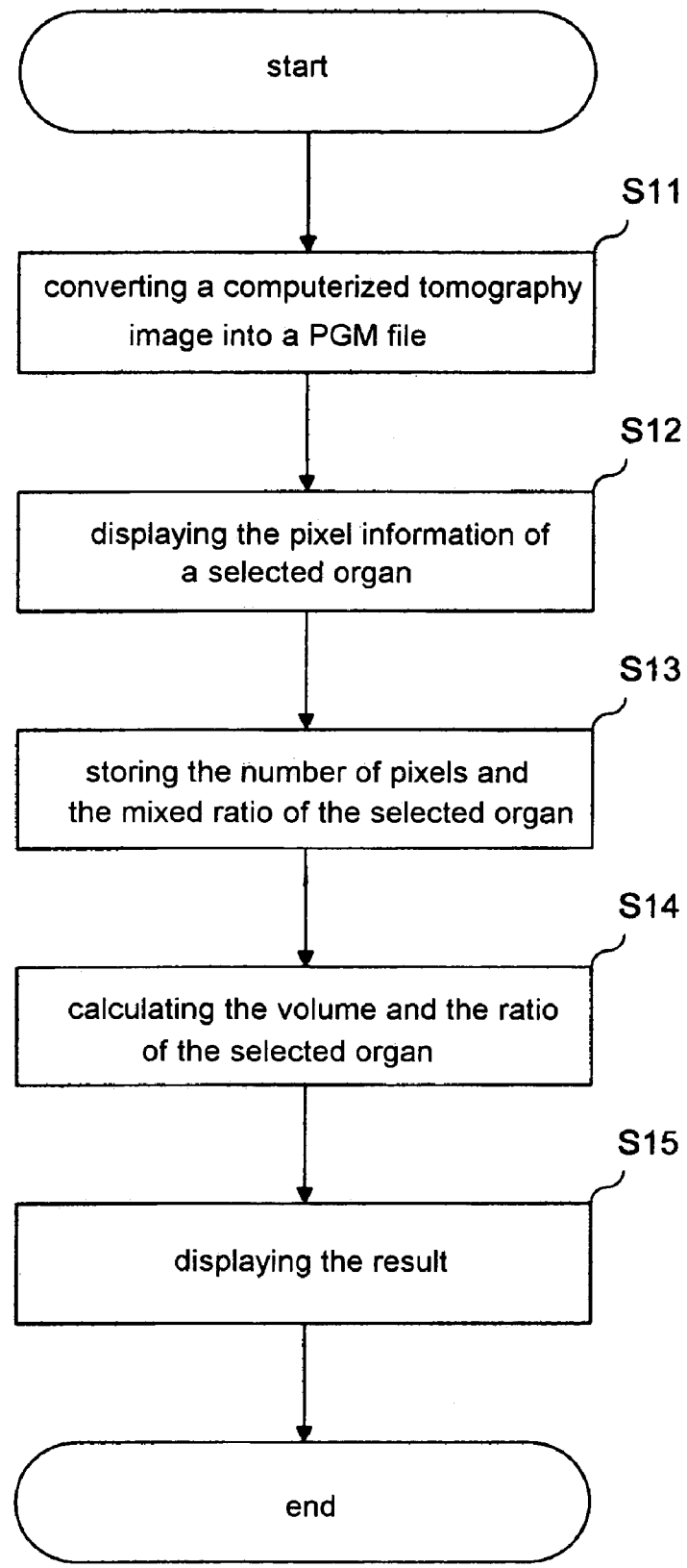
FIG. 15 is a flow diagram illustrating a volume calculation of panniculum according to the present invention.

FIG. 15 is a flow diagram illustrating a volume calculation of panniculum according to the method of the present invention.

A DICOM (Digital Imaging and COmmunications in Medicine) file of an abdomen and legs, which is acquired from computerized tomography apparatus, comprises a header part and an image part. The image part is converted into a PGM(Portable Gray Map) file. The header part contains information such as an identification number, sex and age of the patient, the size of each pixels, distance between slices. The header part, which is converted into a PGM file, comprises several slices and each slice consists of pixels arrayed in a 2D form. If a computerized tomography image is printed on a film, the image is first scanned by a film scanner and then converted into a PGM file. In this case, the header information should be typed by input means such as keyboards S151.

Figure 16:
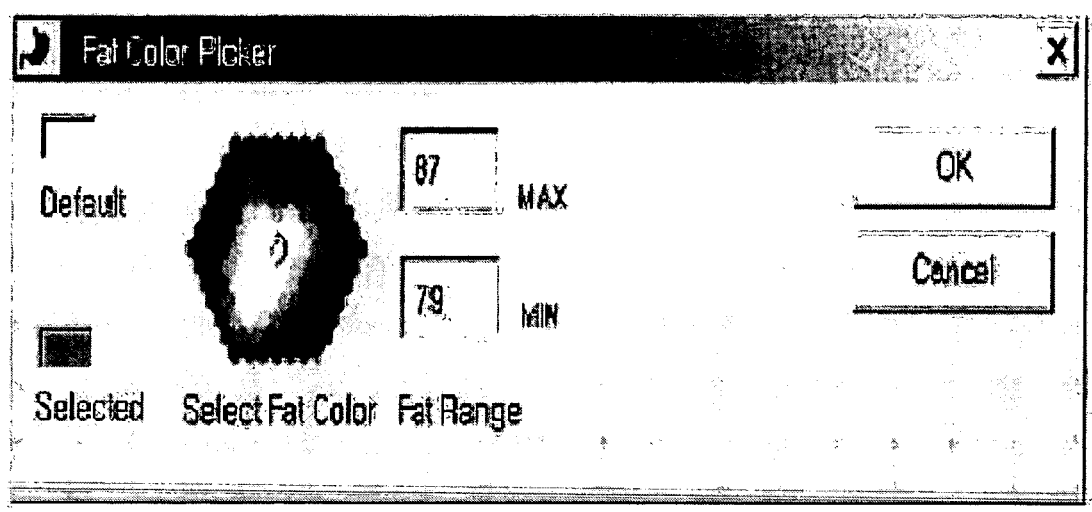
FIG. 16 illustrates a graphic user interface of the present invention.

The pixels having the value of panniculum in a PGM image are found and colored with specific colors. Here, the value of panniculum pixels is in range of 79 to 87 of 256 gray levels, and the value can be changed by a user through graphic user interface unit offered in the system, as seen in FIG. 16. Although the color of panniculum is originally colored yellow, the color can also be changed by a user through the graphic user interface unit offered in the system S152.

For panniculum pixels are mixed with other parts such as muscles, the value of panniculum pixels varies according to the ratio of mixture. Therefore, if the values of genuine panniculum pixels and genuine muscle pixels are known, the relation between the value of panniculum and the ratio of panniculum can be calculated. For example, the value of genuine panniculum pixels is 81 and that of genuine muscle pixels is 91 then the pixel value of a mixture wherein panniculum is 80% and muscle is 20% becomes 83. The values of genuine panniculum pixels and genuine muscle are respectively determined to be the specific parts of panniculum and muscles of a leg. The number of panniculum pixels and the corresponding ratio of the pixels having The CT value of 256 gray levels, which corresponds to the panniculum pixels, and varies according to the mixed ratio of the panniculum and other substances in each slice, are stored in a predetermined memory S153.

Therefore, more accurate volume of panniculum can be calculated using the relation of the value of panniculum and the ratio of panniculum. The formula is as follows. Formula X is a formula wherein all the pixels in range of panniculum values are supposed to be 100% genuine panniculum, and formula Y is a formula wherein each value of panniculum pixels is supposed to contain the corresponding rate of panniculum S154.

V: Volume of a specific organ
PA: Area of a pixel
Psi: Number of pixels in slice i ($1 \leq i \leq n$)
Rj : Ratio of a specific organ to a pixel value j of a specific organ ($Fs \leq j \leq Fe$)
Psij: Number of pixels of which the value of panniculum pixel is j in slice i
Ds: Distance between slices
Fs: First value of the range of pixels of a specific organ
Fe: Last value of the range of pixels of a specific organ
Formula X:

$$V = P_A \left\{ (P_{s1} + P_{sn})\frac{1}{2} + \sum_{i=2}^{n-1} P_{si} \right\} D_s$$

Formula Y:

$$V = P_A \left[ \left\{ \left( \sum_{j=Fs}^{Fe} P_{s1j} R_j \right) + \left( \sum_{j=Fs}^{Fe} P_{snj} R_j \right) \right\} \frac{1}{2} + \sum_{i=2}^{n-1} \left( \sum_{j=Fs}^{Fe} P_{sij} R_j \right) \right] D_s$$

To provide to users these ratios of panniculum graphically, the highest chroma of the panniculum color, which is a yellow or other color selected by a user, becomes the color of 100% genuine panniculum, and as the ratio of panniculum decreases, the chroma becomes lower. Here, changing color is also possible instead of changing chroma S155.

Figure 18:
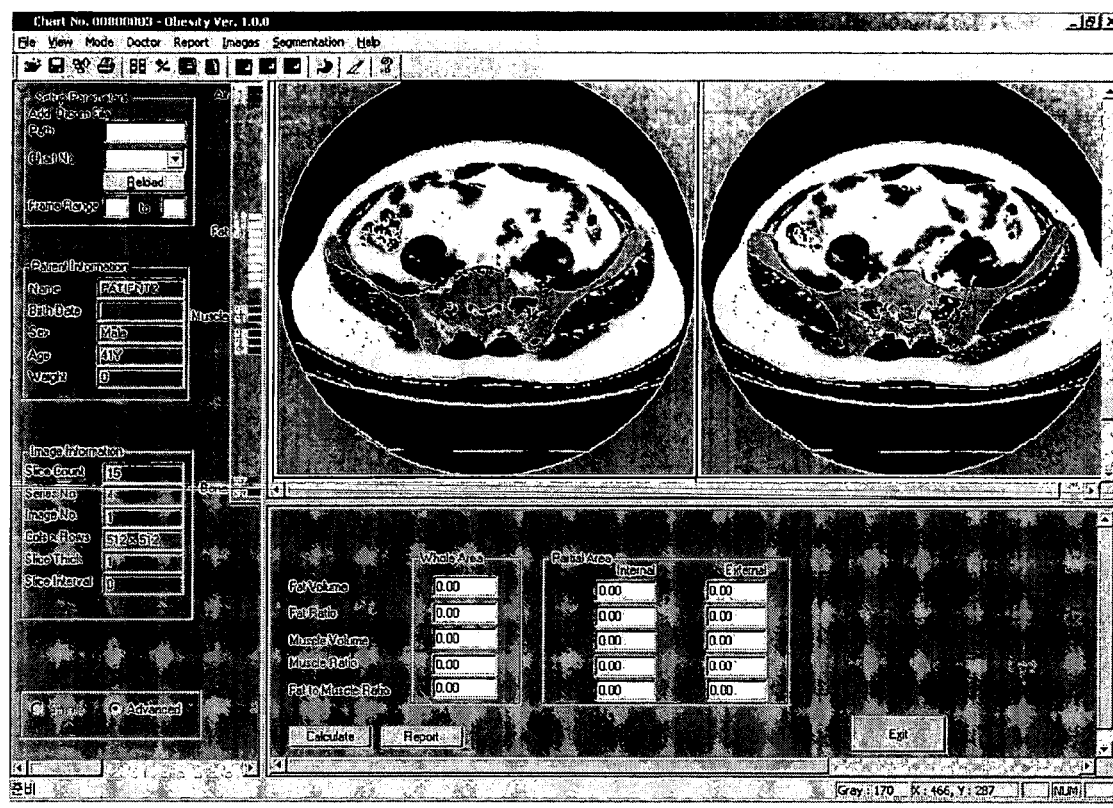
FIG. 18 illustrates the pixels that are differently colored in reference to the ratio of the organ and displayed with a palette.

As a user selects a specific organ in the abdomen with a closed loop line, the selected organ or panniculum contained in the organs is separated from other organs, and the volume and the ratio of panniculum of each selected organ are calculated. As seen in FIG. 17a and FIG. 17b, the volume and the ratio of panniculum in an abdomen image and a leg image are calculated and displayed. Moreover, as seen in FIG. 18, the image consisting of differently colored pixels according to the ratio of panniculum is displayed with a palette.

Likewise, the volume and the ratio of muscles can be accurately calculated from the value of muscle pixels. Therefore, the ratio of panniculum to a muscle from muscles of the same weight can vary, and this ratio represents the degree of fatness.

Figure 20:
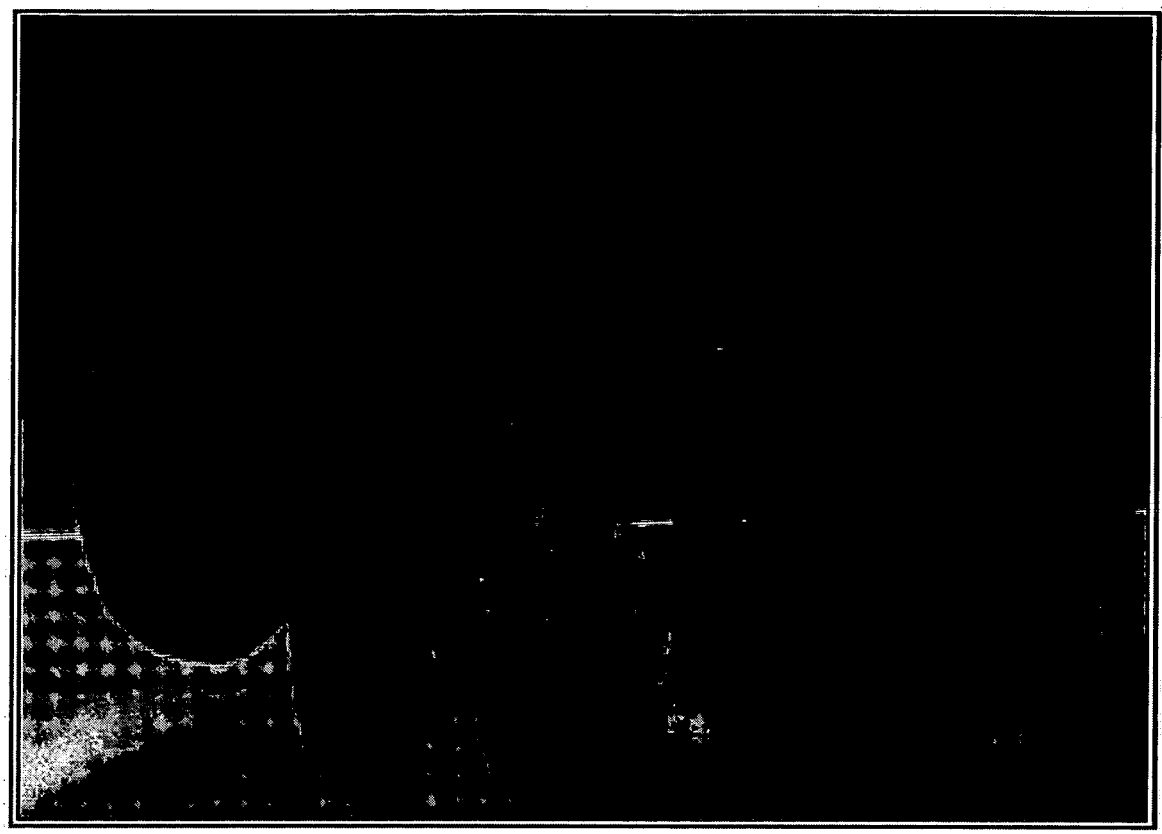
FIG. 20 is a photography of a real liver of a swine.

According to the above formula X, the volume of the liver of a swine, which is extracted from an original image and image-leveled, is 1057.972 ml while the actual volume of the same liver in FIG. 20 is 1055 ml; therefore the accuracy of said formula is proved.

As described above, the medical image processing system of the present invention enables medical people themselves perform image processing without the aid of experts.

What is claimed is:

1. A medical image processing system comprising:
    a medical image storage server for storing digital image data provided by means of computerized tomography or magnetic resonance image apparatus in a medical image database; and
    an image processing system which is coupled to said medical image storage server and to several client computers by TCP/IP protocol;
    wherein said image processing system comprises a user interface unit which converts a user's command into an electric signal and outputs said electric signal;
    an image processor unit which reads a medical image out of said medical image storage server, performs an image processing program comprising a medical image controlling algorithm and outputs a result signal;
    wherein said medical image controlling algorithm comprises both an ordinary digital image processing algorithm and an organ search algorithm and said image processing algorithm further comprises:
    (A) a lung segmentation step which further comprises:
    (a-1) a histogram sliding step in which the gray values of all pixels in an original image are slid by a predetermined offset in order to make the original image brighter;
    (a-2) a thorax segmentation step in which the pixels of the slid image, which are darker than a predetermined gray value, are eliminated;
    (a-3) an equalization step in which said thorax segmented image is converted into a histogram-converted image in order to be distributed in all scales;
    (a-4) an image conversion step in which said thorax segmented image is divided into two parts according to a histogram containing frequencies of values of gray levels wherein the mean value becomes a boundary line;
    (a-5) a boundary extracting step in which only a boundary line of said converted image is extracted in order to eliminate a bronchus image from the lung area;
    (a-6) a boundary tracing step in which right and left lungs are eliminated from the bronchus area along said extracted boundary line;
    (a-7) an image synthesizing step in which the original image and the image of said traced boundary line is synthesized;
    (a-8) an adjusting step in which the thickness of said boundary line is adjusted in order to reduce a difference, which occurs when an inside and an outside of each of right and left lung are recognized; and
    (a-9) a boundary filling step in which an inside and an outside of each of right and left lungs are recognized by assigning predetermined, gray values to the pixels, which is inside said boundary line;
    (B) a step in which said boundary image is enlarged using a morphological filter in order that the lung image contains lung cancer tissue;
    (C) a step in which the pixels having gray values larger than a predetermined value in said lung segmented image are eliminated and the clusters larger than a predetermined number of pixels are selected to be suspected lung cancer tissues;
    (D) a step in which a standard deviation of each pixel is calculated using a histogram of said cluster, which is suspected lung cancer tissue; and
    (E) a lung cancer extracting step in which a lung cancer tissue is distinguished from the partial volume; and
    an output interface unit which receives said result signal and converts said result signal into a format which user can recognize.

2. The medical image processing system of claim 1, wherein said image processing system transfers said result image to each client computer and relays information among said client computers.

3. A medical image processing method for extracting a lung cancer image comprising the steps of:
    providing a menu screen as a window frame on a display means;
    converting a command of a user, which is received through an input interface unit, into a control signal and transferring said control signal to an image processor unit; analyzing said control signal; loading an image corresponding to said control signal and displaying said image on the display means;
    receiving an image processing control signal from the user;
    reading an image processing algorithm embedded in said image processor and performing said algorithm,
    wherein said medical image controlling algorithm comprises both an ordinary digital image processing algorithm and an organ search algorithm and said image processing algorithm further comprises:
    (A) a lung segmentation step which further comprises:
    (a-1) a histogram sliding step in which the gray values of all pixels in an original image are slid by a predetermined offset in order to make the original image brighter;
    (a-2) a thorax segmentation step in which the pixels of the slid image, which are darker than a predetermined gray value, are eliminated;
    (a-3) an equalization step in which said thorax segmented image is converted into a histogram-converted image in order to be distributed in all scales;
    (a-4) an image conversion step in which said thorax segmented image is divided into two parts according to a histogram containing frequencies of values of gray levels wherein the mean value becomes a boundary line;
    (a-5) a boundary extracting step in which only a boundary line of said converted image is extracted in order to eliminate a bronchus image from the lung area;

(a-6) a boundary tracing step in which right and left lungs are eliminated from the bronchus area along said extracted boundary line;

(a-7) an image synthesizing step in which the original image and the image of said traced boundary line is synthesized; (a-8) an adjusting step in which the thickness of said boundary line is adjusted in order to reduce a difference, which occurs when an inside and an outside of each of right and left lung are recognized; and (a-9) a boundary filling step in which an inside and an outside of each of right and left lungs are recognized by assigning predetermined, gray values to the pixels, which is inside said boundary line;

(B) a step in which said boundary image is enlarged using a morphological filter in order that the lung image contains lung cancer tissue;

(C) a step in which the pixels having gray values larger than a predetermined value in said lung segmented image are eliminated and the clusters larger than a predetermined number of pixels are selected to be suspected lung cancer tissues;

(D) a step in which a standard deviation of each pixel is calculated using a histogram of said cluster, which is suspected lung cancer tissue; and (E) a lung cancer extracting step in which a lung cancer tissue is distinguished from the partial volume; and displaying a result image acquired by performing said algorithm on a display means; and storing result data, which is obtained according to the command of the user, in a specific storage server.

4. The medical image processing method of claim 3, wherein said result image displayed on said display means comprises organ images, each of which has a unique color and a plurality of pixels, and a palette according to a ratio of the volume of the organ.

5. The medical image processing method of claim 3, wherein said ordinary digital image processing algorithm comprises an image-leveling algorithm and an image-coloring algorithm.

6. The medical image processing method of claim 5, wherein the volume calculation of said organ-searching algorithm is calculated by a formula which is [area of one pixel×(((number of pixels having the first CT value of CT values of an organ in first slice)×(corresponding ratio)+ . . . +number of pixels having the last CT value of CT values of an organ in first slice×corresponding ratio)+(number of pixels having the first CT value of CT values of an organ in last slice×corresponding ratio+ . . . +number of pixels having the last CT value of CT values of an organ in last slice×corresponding ratio)×½+(number of pixels having the first CT value of CT values of an organ in the second slice to the second to last slice×corresponding ratio+ . . . +number of pixels having the last CT value×corresponding ratio)×a distance between slices).

* * * * *